United States Patent [19]

Vargas et al.

[11] Patent Number: 5,411,734
[45] Date of Patent: May 2, 1995

[54] NON-IRRITATING α-HYDROXY CARBOXYLIC ACID COMPOSITIONS

[75] Inventors: Anthony Vargas, Monroe; Pamela C. Asplund, Shelton; Cathleen Corcoran, Bridgeport, all of Conn.

[73] Assignee: Elizabeth Arden Company, Division of Conopco, Inc., New York, N.Y.

[21] Appl. No.: 152,152

[22] Filed: Nov. 15, 1993

[51] Int. Cl.$^6$ .................. A61K 7/00; A61K 31/19
[52] U.S. Cl. ................... 424/401; 514/557; 514/847; 514/937
[58] Field of Search ............... 424/401, 78.03; 514/937, 557, 847

[56] References Cited

U.S. PATENT DOCUMENTS

| | | |
|---|---|---|
| 4,105,782 | 8/1978 | Yu et al. ............... 424/283 |
| 4,105,783 | 8/1978 | Yu et al. ............... 424/283 |
| 4,197,316 | 8/1980 | Yu et al. ............... 424/317 |
| 4,234,599 | 11/1980 | Van Scott et al. ............... 424/279 |
| 4,424,234 | 1/1984 | Alderson et al. ............... 424/317 |
| 4,746,509 | 5/1988 | Haggiage ............... 424/449 |
| 5,021,185 | 6/1991 | Muskakallio ............... 252/142 |
| 5,091,171 | 2/1992 | Yu et al. ............... 424/642 |

*Primary Examiner*—Thurman K. Page
*Assistant Examiner*—Sally Gardner
*Attorney, Agent, or Firm*—Milton L. Honig

[57] ABSTRACT

A cosmetic composition is provided which includes as an active ingredient a $C_2$–$C_{28}$ α-hydroxy carboxylic acid within a non-stinging ester base formula comprising a $C_7$–$C_{60}$ neoalkanol ester and a $C_{12}$–$C_{40}$ fatty acid ester alkoxylated with from 1 to 100 moles alkylene oxide per mole of glyceride.

3 Claims, No Drawings

NON-IRRITATING α-HYDROXY CARBOXYLIC ACID COMPOSITIONS

BACKGROUND OF THE INVENTION

1. Field of the Invention

The invention concerns a cosmetic composition including a $C_2$–$C_{28}$ α-hydroxy carboxylic acid present in a non-irritating carrier.

2. The Related Art

A soft, supple and flexible skin has a marked cosmetic appeal and is an attribute of normal functioning epidermis. As human skin ages with advancing years, the epidermis can become folded, ridged or furrowed to form wrinkles. These signal of loss of youthful appearance and herald the transition to old age. Exposure to excessive doses of sunlight accelerates the transition process. Also, the outer layer of the epidermis known as the stratum corneum can become dry and flaky following exposure to cold weather or excessive contact with detergents or solvents. Loss of skin moisture thereby results and the skin begins to lose the soft, supple and flexible characteristics.

Emollients such as fats, phospholipids and sterols have in the past been used to soften wrinkled or dry skin. These emollients are only partially effective as a remedy for skin in poor condition.

The use of α-hydroxy carboxylic acids for enhancing the quality of human skin has been known for some time. There is no doubt that α-hydroxy carboxylic acids are therapeutically effective much beyond the common emollients.

U.S. Pat. No. 4,424,234 (Alderson et al.) discloses skin treatment compositions incorporating α-hydroxycaproic acid and α-hydroxycaprylic acid or mixtures thereof in compositions that have a pH value of less than 7, usually from 2 to 4. Yu and Van Scott have patented widely in this area. For instance, U.S. Pat. No. 4,105,782 reports amines or ammonium salts of α-hydroxy carboxylic acids in the treatment of acne or dandruff. In U.S. Pat. No. 4,105,783 and U.S. Pat. No. 4,197,316, these compounds are suggested for the treatment of dry skin. U.S. Pat. No. 4,234,599 discloses the use of α-hydroxy carboxylic acids, their esters or amine salts in the treatment of keratoses. More recently, U.S. Pat. No. 5,091,171 focused attention on these compounds as being effective against age spots, wrinkles and aging relative skin changes.

While α-hydroxy carboxylic acids hold much therapeutic promise, these materials have been found to irritate human skin on repeated topical applications. The irritation may range from a sensation of tingling, itching and burning to clinical signs of redness and peeling. Causes for such irritation have been linked to the lowering of pH in the stratum corneum of human skin. Low pH has been suggested as provoking disturbances in intercorneocyte bondings resulting in adverse skin reactions, specially in some individuals with sensitive skin.

Accordingly, it is an object of the present invention to provide a composition including α-hydroxy carboxylic acids with a carrier formulation that avoids irritation including the sensation of tingling, itching and burning as well as any clinical signs of redness and peeling.

This object and others will become more evident through consideration of the following summary, detailed description and examples which follow.

SUMMARY OF THE INVENTION

A cosmetic composition is provided which includes:
(i) from about 0.0001 to about 20% of a $C_2$–$C_{28}$ α-hydroxy carboxylic acid; and
(ii) from about 30 to about 95% by weight of an ester carrier base comprising:
  (a) from about 1 to about 90% of a $C_7$–$C_{60}$ neoalkanol ester; and
  (b) from about 1 to about 90% of a $C_{12}$–$C_{40}$ fatty glyceride ester alkoxylated with from 1 to 100 moles $C_2$–$C_3$ alkylene oxide per mole of glyceride.

Advantageously, the ester carrier may also include a polyglyceryl $C_8$–$C_{22}$ fatty acid ester such as polyglyceryl-6 dioleate. Simple esters such as $C_3$–$C_{22}$ alkanol esters of $C_8$–$C_{22}$ alkanoic acids may also be included as components of the ester base.

Emulsifiers may also be present. These may be polyalkoxylated ethers of $C_8$–$C_{22}$ alkanols or $C_{10}$–$C_{22}$ fatty acid esters of glycerine.

While the invention generically focuses upon α-hydroxy carboxylic acids, the most preferred are the L stereoisomer forms in distinction to the D and racemic forms. Most preferred is l-lactic acid.

Active compounds other than α-hydroxy carboxylic acids may also be included. Chief among such compounds are the ceramides which are N-acylated sphingosine bases. Especially preferred are Ceramide 2 and Ceramide 3.

DETAILED DESCRIPTION

Irritation and stinging attributed to $C_2$–$C_{28}$ α-hydroxy carboxylic acids have now been found to be considerably reduced through formulation of the acids in an ester base constituting the major constituent of the cosmetic composition. More precisely, the ester base will be present at levels of at least 30% up to 95%, preferably from 45% to 80%, optimally from 50 to 70% by weight. The ester base will be constituted of a $C_7$–$C_{60}$ neoalkanol ester and a $C_{12}$–$C_{40}$ fatty glyceride ester alkoxylated with from 1 to 100 moles alkylene oxide per mole of glyceride.

The $C_7$–$C_{60}$ neoalkanol ester will normally be present in an amount from 1 to 90%, preferably from 20 to 75%, optimally from 30 to 50% by weight of the composition. Illustrative of this category are esters formed from the reaction between $C_1$–$C_{22}$ alkanoic acid with either neopentyl alcohol, neopentyl glycol, 2-butyl-2-ethyl-1,3-propane diol, 2,2,4-trimethyl-1,3-pentane diol, trimethylol propane, pentaerythritol, ditrimethylol propane, di-pentaerythritol or pentaerythritol-trimethylol propane dimers. Examples include isostearyl neopentanoate, palmityl neopentanoate, tetraoctyl pentaerythritol and diisopropyl neopentanoate. Most preferred is isostearyl neopentanoate.

The $C_{12}$–$C_{40}$ fatty glyceride ester alkoxylate will include from 1 to 100 moles alkylene oxide per mole of glyceride, preferably from 4 to 20 moles alkylene oxide per mole of glyceride. The preferred alkylene oxides are ethylene oxide and propylene oxide. Amounts of this ester may range from 1 to 90%, preferably from 5 to 50%, optimally from 10 to 20% by weight of the composition. Illustrative of this category are PEG-6 caprylic/capric glyceride and PEG-8 caprylic/capric glyceride each of which are polyethylene glycol derivatives of a mixture of mono, di and triglycerides of caprylic and capric acids with a respective 6 and 8 moles of ethylene oxide. The higher alkoxylated ester is available from Gattefosse sold under the trademark of Labrasol.

Advantageously, the ester base of the present composition may further include a polyglycerol $C_8$–$C_{22}$ fatty acid ester. Amounts of this ester may range from 1 to 50%, preferably from 5 to 25%, optimally from 10 to 20% by weight of the composition. Illustrative of this category are polyglycerol-3 beeswax, polyglycerol-4 cocoate, polyglycerol-10 decalinoleate, polyglycerol-10 decaoleate, polyglycerol-7 decastearate, polyglycerol-2 diisostearate, polyglycerol-3 diisostearate, polyglycerol-7 diisostearate, polyglycerol-2 dioleate, polyglycerol-3 dioleate, polyglycerol-6 dioleate, polyglycerol-10 dioleate, polyglycerol-3 distearate, polyglycerol-6 distearate, polyglycerol-10 distearate, polyglycerol-10 heptaoleate, polyglycerol-10 heptastearate, polyglycerol-6 hexaoleate, polyglycerol-2 isostearate, polyglycerol-4 isostearate, polyglycerol-6 isostearate, polyglycerol-10 laurate, polyglycerol-10 myristate, polyglycerol-2 oleate, polyglycerol-3 oleate, polyglycerol-4 oleate, polyglycerol-6 oleate, polyglycerol-8 oleate, polyglycerol-10 oleate and combinations thereof. Most preferred is polyglycerol-6 dioleate which is a diester of oleic acid and a glycerin polymer containing an average of 6 glycerin units, available from Gattefosse under the trademark Plurol Oleique WL 1173.

A still further component of the ester base may be simple $C_3$–$C_{22}$ alkanol esters of $C_8$–$C_{22}$ alkanoic acids. Amounts of this material may range from 1 to 50%, preferably from 5 to 30%, optimally from 10 to 20% by weight of the cosmetic composition. Illustrative of this category are cetyl octanoate, lauryl pentanoate, palmityl palmitoate, isostearyl decanoate, oleyl heptanoate and combinations thereof. Most preferred are cetyl octanoate, available under the trademark Trivent OC-16.

A wide variety of α-hydroxy carboxylic acids may be employed for purposes of the present invention. Suitable examples include:

α-hydroxyethanoic acid
α-hydroxypropanoic acid
α-hydroxyhexanoic acid
α-hydroxyoctanoic acid
α-hydroxydecanoic acid
α-hydroxydodecanoic acid
α-hydroxytetradecanoic acid
α-hydroxyhexadecanoic acid
α-hydroxyoctadecanoic acid
α-hydroxyeicosanoic acid
α-hydroxydocosanoic acid
α-hydroxyhexacosanoic acid, and
α-hydroxyoctacosanoic acid Particularly preferred from the above list are α-hydroxyethanoic acid (commonly known as glycolic acid), α-hydroxypropanoic acid (commonly known as lactic acid) and α-hydroxyoctanoic acid (commonly known as α-hydroxycaprylic acid or HCA).

For purposes of this invention, the term α-hydroxy carboxylic acids are intended to include not only the acid form but also salts thereof. Typical salts are the alkalimetal, ammonium and $C_2$–$C_{30}$ ammonium salts thereof. Particularly preferred are the sodium, potassium, triethanolammonium and ammonium salts. Combinations of all the foregoing may be present in the compositions.

Amounts of the α-hydroxy carboxylic acid will range from 0.001 to 20%, preferably from 0.01 to 15%, optimally from 0.5 to 10% by weight of the cosmetic composition.

Skin active agents other than α-hydroxy carboxylic acids may also be included in compositions of the present invention. These actives may include sunscreens, tanning agents, anti-acne agents and adjunct anti-wrinkle inhibitors. Among the latter category are ceramides which are N-acylated sphingosine bases. Especially preferred are ceramide 1, ceramide 2 and ceramide 3. Identity of these materials are well-outlined in "Advances in Lipid Research," Vol. 24, pgs. 27–56, by Schurer and Elias (1991). Levels of ceramide may range from 0.00001 to 1% by weight.

Vitamins may also be included in the compositions of the present invention. Especially preferred is vitamin A palmitate (retinyl palmitate) and vitamin E linoleate (tocopheryl linoleate). Other esters of vitamins A and E may also be utilized.

Compositions of the present invention are preferably anhydrous (less than 2% but preferably less than 0.5% water) but may also be aqueous. When water is present, the product form may be as an emulsion in the form of a lotion or cream.

Among other types of pharmaceutically acceptable carriers may be silicone oils. Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms.

Linear volatile silicone materials generally have viscosities less than about 5 centistokes at 25° C. while cyclic materials typically have viscosities of less than about 10 centistokes.

Examples of preferred volatile silicone oils useful herein include: Dow Corning 344, Dow Corning 345 and Dow Corning 200 (manufactured by Dow Corning Corp.); Silicone 7207 and Silicone 7158 (manufactured by the Union Carbide Corp.); SF 1202 (manufactured by General Electric); and SWS-03314 (manufactured by SWS Silicones, Inc.).

The nonvolatile silicone oils useful in compositions of this invention are exemplified by the polyalkyl siloxanes, polyalklyaryl siloxanes and polyether siloxane copolymers. The essentially nonvolatile polyalkyl siloxanes useful herein include, for example, polydimethyl siloxanes with viscosities of from about 5 to about 100,000 centistokes at 25° C. Among the preferred nonvolatile silicones useful in the present compositions are the polydimethyl siloxanes having viscosities from about 10 to about 400 centistokes at 25° C. Such polyalkyl siloxanes include the Viscasil series (sold by General Electric Company) and the Dow Corning 200 series (sold by Dow Corning Corporation). Polyalkylaryl siloxanes include poly(methylphenyl)siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corporation). Useful polyether siloxane copolymers include, for example, a polyoxyalkylene ether copolymer having a viscosity of about 1200 to 1500 centistokes at 25° C. Such a fluid is available as SF-1066 organosilicone surfactant (sold by General Electric Company). Cetyl dimethicone copolyol and cetyl dimethicone are especially preferred because these materials also function as emulsifiers and emollients.

Silicones may be present in amounts ranging from about 0.1 up to about 60%, preferably from about 2 to about 25%, optimally between about 10 and 20% by weight.

Fatty alcohols and fatty acids having from 10 to 20 carbon atoms may also be included in compositions of the present invention. Especially preferred are such compounds as cetyl, myristyl, palmityl, isostearyl and stearyl alcohols and acids.

Emulsifiers may also be incorporated into cosmetic compositions of the present invention. These emulsifiers may range from 0.5 to 30%, preferably from 1 to 15%, optimally from 3 to 8% by weight. Emulsifiers may be nonionic, anionic, cationic or amphoteric in nature and combinations thereof may be employed.

Most preferred for purposes of this invention are the emulsifiers PPG-5-ceteth-20 which is a polyoxypropylene-polyoxyethylene ether of cetyl alcohol commercially available from Croda under the trademark Procetyl AWS and glycerol monoisostearate commercially available from the Scher Chemical Company under trademark Schercemol GMIS.

Cosmetic compositions of the present invention are preferably clear (transparent) for aesthetic and functional reasons. Clarity is achieved through formulation as a microemulsion with particle size of each droplet ranging from about 0.001 to about 0.2 microns in diameter.

Another category of functional ingredient within the cosmetic compositions of the present invention are thickeners. A thickener will usually be present in amounts anywhere from 0.1 to 20% by weight, preferably from about 0.5 to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Many cosmetic compositions, especially those containing water, must be protected against the growth of potentially harmful microorganisms. Preservatives are, therefore, necessary. Suitable preservatives include alkyl esters of p-hydroxybenzoic acid, hydantoin derivatives, proprionate salts, and a variety of quaternary ammonium compounds.

Particularly preferred preservatives are methyl paraben, propyl paraben, imidazolidinyl urea, sodium dehydroxyacetate and benzyl alcohol. Preservatives will usually be employed in amounts ranging from about 0.1% to 2% by weight of the composition.

Powders may be incorporated into the cosmetic compositions of the invention. These powders include chalk, talc, Fullers earth, kaolin, starch, smectites clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these materials may range anywhere from 0.001 up to 20% by weight of the composition.

The following examples will more fully illustrate selected embodiments of this invention. All parts, percentages and proportions referred to herein and in the appended claims are by weight unless otherwise indicated.

EXAMPLE 1

This example illustrates a series of cosmetic compositions according to the present invention.

TABLE I

| COMPONENT | FORMULA (WT. %) | | | | |
|---|---|---|---|---|---|
| | 1 | 2 | 3 | 4 | 5 |
| l-Lactic Acid | 2.00 | 3.00 | 4.00 | 5.00 | 4.00 |
| Potassium l-Lactate | 0.93 | 1.41 | 1.88 | 2.34 | 1.68 |
| Isostearyl Neopentanoate | 36.50 | 35.01 | 33.54 | 32.08 | 20.83 |
| PEG-8 Caprylic/Capric Glycerides | 14.30 | 14.30 | 14.30 | 14.30 | 14.30 |
| Cetyl Octanoate | 12.75 | 12.75 | 12.75 | 12.75 | 15.88 |
| Polyglyceryl-6 Dioleate | 11.90 | 11.90 | 11.90 | 11.90 | 11.90 |
| Cyclomethicone | 10.17 | 10.17 | 10.17 | 10.17 | 20.33 |
| PPG-5-Ceteth-20 | 5.10 | 5.10 | 5.10 | 5.10 | 5.10 |
| Glyceryl Isostearate | 3.13 | 3.13 | 3.13 | 3.13 | — |
| Hydroxycaprylic Acid | 0.01 | 0.01 | 0.01 | 0.01 | — |
| Ceramide 3 | 0.01 | 0.01 | 0.01 | 0.01 | — |
| Ceramide 2 | 0.01 | 0.01 | 0.01 | 0.01 | — |
| Isostearic Acid | — | — | — | — | 3.13 |
| Vitamin A Palmitate | — | — | — | — | 1.00 |
| Vitamin E Linoleate | — | — | — | — | 0.20 |
| Water | qs | qs | qs | qs | qs |

EXAMPLE 2

A further pair of cosmetic compositions were formulated to evaluate stinging and/or burning potential when applied to the face. Table II outlines the formulas utilized in the clinical test.

TABLE II

| COMPONENT | PRODUCT (WEIGHT %) | |
|---|---|---|
| | 1 | 2 |
| l-Lactic acid | 5.0 | — |
| Isostearyl Neopentanoate | 18.8 | 18.8 |
| PEG-8 Caprylic/Capric Glycerides | 17.6 | 17.6 |
| Polyglyceryl-6 Dioleate | 14.7 | 14.7 |
| Cetyl Octanoate | 14.8 | 14.8 |
| Cyclomethicone | 8.0 | 8.0 |
| Squalene | 5.0 | 5.0 |
| PPG-5-Ceteth-20 | 6.3 | 6.3 |

Sixteen panelists, previously screened as lactic acid "stingers" were recruited for the study. Both males and females were enrolled, ranging in age from 25 to 55. The study took place over a two day period. Panelists were instructed to remove make-up on their faces by washing with soap and water at least one hour prior to test time. At the test time, each panelist washed the cheek area with Cetaphil®, a gentle cleanser. Then faces were padded dry with a paper towel. After a five minute rest period, 0.05 cc of test product was applied to a weighing boat via tuberculin syringe (without a needle). The product was rubbed into the test site for 20 seconds using a finger cot.

Each test product was generously applied, to the nasolabial folds and cheeks of eight panelists. The subjects were questioned about stinging responses at 10 seconds, 2.5 minutes, 5.0 minutes and 8.0 minutes after product application. The following scale was used:

0 = no stinging
1 = light discomfort
2 = moderate discomfort
3 = severe stinging/burning Two products were evaluated on a panelist, one on each side of the face. A randomization schedule was employed.

Stinging was evaluated at 10 second, 2.5 minutes, 5.0 minutes and 8.0 minutes on an 4-point scale. Some substances may cause slight to severe stinging immediately after application with disappearance of the sensation within 5 to 30 seconds. Delayed stinging generally is not preceded by a transient phase and usually becomes evident within a minute or two. The delayed stinging score for an individual is the mean of the three readings at 2.5, 5.0 and 8.0 minutes. Substances with average scores falling between 0.4 and 1.0 have a slight stinging potential. The range 1.1 to 2.0 signifies moderate stinging, and 2.1 to 3.0 denotes severe stinging.

The Overall Average stinging response for the 5.0% lactic acid Product 1 was 0.17. This must be compared with the Overall Average for the control Product 2 which was 0.00. Since Product 1 presented a stinging response of less than 0.4, it is classified as having less than a slight potential for stinging during routine usage. Ordinarily, compositions with 5% lactic acid are substantially stinging. The sting inhibitory response is attributed to the nature of the ester base carrier.

The foregoing examples illustrated only selected embodiments of the present invention and should be considered nonlimiting examples with variations and modifications thereof all being within the spirit and purview of this invention.

What is claimed is:

1. A cosmetic composition comprising:
   (i) from about 0.0001 to about 20% of a $C_2$–$C_{28}$ α-hydroxy carboxylic acid selected from the group consisting of glycolic acid, lactic acid and combinations thereof; and
   (ii) from about 30 to about 95% by weight of an ester carrier base comprising:
      (a) from about 1 to about 90% of a $C_7$–$C_{60}$ neoalkanol ester;
      (b) from about 1 to about 90% of a $C_{12}$–$C_{40}$ fatty glyceride ester alkoxylated with from 1 to 100 moles $C_2$–$C_3$ alkylene oxide per mole of glyceride; and
      (c) from 1 to 50% of a polyglycerol $C_8$–$C_{22}$ fatty acid ester.

2. A cosmetic composition according to claim 1, further comprising as a component of the ester carrier base a $C_3$–$C_{22}$ alkanol ester of a $C_8$–$C_{22}$ alkanoic acid in an amount from 1 to 50% by weight.

3. A cosmetic composition according to claim 1 which is anhydrous.

* * * * *